US00PP13779P29

(12) United States Plant Patent
Diboll

(10) Patent No.: US PP13,779 P2
(45) Date of Patent: May 6, 2003

(54) HELIOPSIS PLANT NAMED 'PRAIRIE SUNSET'

(76) Inventor: Neil Hart Diboll, P.O. Box 306, Westfield, WI (US) 53964-0306

( * ) Notice: Subject to any disclaimer, the term of this patent is extended or adjusted under 35 U.S.C. 154(b) by 0 days.

(21) Appl. No.: 10/000,102

(22) Filed: Dec. 4, 2001

(51) Int. Cl.[7] ..... A01H 5/00

(52) U.S. Cl. ..... Plt./263
(58) Field of Search ..... Plt./263

*Primary Examiner*—Bruce R. Campell
*Assistant Examiner*—Anne Marie Grünberg
(74) *Attorney, Agent, or Firm*—Penny J. Aguirre

(57) ABSTRACT

A new cultivar of *Heliopsis helianthoides* 'Prairie Sunset' characterized by its purple-veined foliage, purple stems, and yellow ray flowers that emerge with distinct red coloration on the basal portion of the petals.

3 Drawing Sheets

BACKGROUND OF THE INVENTION

The present invention relates to a new and distinct cultivar of *Heliopsis helianthoides* and will be referred to hereafter by its cultivar name, 'Prairie Sunset'. 'Prairie Sunset' represents a new Ox Eye Sunflower, an herbaceous perennial grown for landscape use.

The inventor discovered the new cultivar, 'Prairie Sunset', in a cultivated field in Westfield, Wis. in the summer of 1994. The inventor collects and sows seed of *Heliopsis helianthoides* for commercial seed production. 'Prairie Sunset' was discovered as a mutant seedling in a cultivated production field. The new cultivar was selected from seedlings produced by open-pollination of *Heliopsis helianthoides.* No named cultivars of *Heliopsis helianthoides* were grown in the production field.

The combined characteristics of 'Prairie Sunset': its purple-veined foliage, sturdy purple stems, and yellow ray flowers with distinct red coloration on the basal portion of the petals. These characteristics make this new cultivar unique and unlike any other known cultivars of *Heliopsis helianthoides* known to the inventor. Although there are cultivars that exist with variation in flower color and form, no cultivars known to the inventor have ray flowers with red basal coloration.

Asexual reproduction of the new cultivar was first accomplished by division in Westfield, Wis. in spring of 1995 by the inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Prairie Sunset' from other varieties in commerce known to the inventor.

1. Foliage is deep green with veins that have purple coloration.

2. Purple stems are sturdy and wind tolerant.

3. Yellow flowers have red coloration on the basal portion of the petals when they emerge. The red coloration fades to a red-orange after approximately ten days and then gradually fades to yellow as the flower continues to age.

4. Long blooming; blooming for up to 12 weeks in mid-summer and early fall.

5. Tolerant to a wide range of growing conditions, growing well in full sun to light shade in dry to moist soils.

BRIEF DESCRIPTION OF THE DRAWING

The plants and plant parts in the Figures depict a two-year old plant grown from a root division of 'Prairie Sunset' in an outdoor trial bed in Westfield, Wis.

FIG. One shows the plant habit when in peak bloom.

FIG. Two shows a close-up of a flower and the purple stems of the new invention.

FIG. Three is a close-up of the foliage and flowers as they mature. The flower on the right has been open for 10 days and the center color has faded to a lighter red color. The flower on the left has been open for 16 days and the center color has almost completely faded to that of the rest of the petals. The vein coloration on the foliage can also be observed in FIG. Two. The colors in the photographs are as close as possible with conventional photography.

BOTANICAL DESCRIPTION OF THE PLANT

The following is a detailed description of the new cultivar as grown in a trial bed for two years in Westfield, Wis. The phenotype of the new cultivar may vary with variations in environmental, climatic, and cultural conditions, as it has not been tested under all possible environmental conditions. The color determination is in accordance with the 1995 R.H.S. Colour Chart of The Royal Horticultural Society, London, England, except where general color terms of ordinary dictionary significance are used.

Botanical classification: 'Prairie Sunset' is a cultivar of *Heliopsis helianthoides.*
Commercial classification: Ox Eye Sunflower.
Parentage: Seedling from open pollination of *Heliopsis helianthoides.*
General description:
- *Blooming period.*—About 12 weeks in mid-summer to early fall, between July and September.
- *Plant habit.*—Herbaceous perennial. Clump-forming, upright, loosely but freely branched. Vigorous grower.

*Height and spread.*—Up to 0.6 m in width and up to 1.8 m in height.

*Hardiness.*—Zone 4–8.

*Culture.*—Tolerant to a wide range of growing conditions, growing well in full sun to light shade, in dry to moist soils.

*Diseases and pests.*—*Heliopsis helianthoides* is relatively disease free. No susceptibility or resistance to diseases or pests has been observed for 'Prairie Sunset'.

*Root description.*—Fibrous, fine and well-branched.

Growth and propagation:

*Propagation.*—Division, vegetative terminal and internode stem cuttings, and tissue culture.

*Root initiation.*—10 to 14 days at 70° F. air temp in summer.

*Time required for root development.*—8 weeks to fully develop in a 32 cell in soil-less media when grown at 70–80° F. in a greenhouse without supplemental lighting in summer.

Stem description:

*Shape.*—Round, solid.

*Stem color.*—New growth; 144B, 187A. Mature growth: intermediate between 187A and 166A (more brown).

*Stem size.*—Approximately 5 mm in diameter with lateral branches 2 to 3 mm in diameter.

*Stem surface.*—Mature stems are glabrous; stems of new growth have fine white hairs.

*Internode length.*—5.0 to 9.0 cm in length.

*Branching.*—Loosely branched.

Foliage description:

*Leaf shape.*—Ovate.

*Leaf division.*—*Simple.*

*Leaf base.*—Cuneate.

*Leaf apex.*—Acute.

*Leaf venation.*—Tri-nerved, center vein on upper surface is a greyed-purple in color (184B) and typically extends two-thirds of the distance from the base.

*Leaf margins.*—Serrate.

*Leaf attachment.*—Petiolate.

*Leaf arrangement.*—Opposite.

*Leaf surface.*—Upper; scabrous. Lower; very fine, short hairs.

*Leaf color.*—Immature: upper; 147A, lower; 147B. Mature: upper; Intermediate between 137A and 139A, lower; 138A.

*Petiole size.*—3 to 6 mm in length, 1.0 to 1.5 mm in width.

*Petiole shape.*—Rounded on lower surface and flat on upper surface.

*Petiole color.*—166A in color.

Flower description:

*Type.*—Capitulum: heterogamous with ray florets around the head margin and disk florets in the center, forming a radiant head. Single capitulum per terminal arising from leaf axils.

*Lastingness of inflorescence.*—About 30 days until senescence of ray flowers. Disk flowers are persistent.

*Capitulum size.*—About 1 cm in depth and 3.5 to 4.5 cm in diameter.

*Fragrance.*—None.

Involucral bracts or phyllary (often referred to as the calyx):

*Bract number.*—12–18 in 2 overlapping rows.

*Calyx size.*—8 to 10 mm in length and 3–4 mm in width. Fused at base.

*Calyx color.*—138B in color with 3 mm tips 137A.

*Texture.*—Pubescent.

*Bract apex.*—Acute.

*Bract shape.*—Oblong.

*Buds.*—Cup-shaped, up to 8 mm in diameter, phyllary are 138B in color, and the tips of the disk flowers are 183B just prior to opening.

*Peduncle.*—Flexible, 7 to 9 cm in length and about 2 mm in diameter, 187A in color, texture is pubescent with very fine hairs.

Ray florets (gynoecium only):

*Number.*—8 to 14.

*Shape.*—Oblong with 2 recessed ribs running vertically.

*Size.*—1.1–1.8 mm in length and 0.7 to 1.1 mm in width.

*Apex.*—Retuse.

*Base.*—Attenuate.

*Margins.*—Entire.

*Aspect.*—Flat.

*Texture.*—Glabrous.

*Color.*—Upper; opens 15A mature to 7A, lower; opens 15B, matures to 7B. Basal red portion of ray flowers: Upper surface only, 46A for approximately 10 days after opening, then fading to 47B for approximately 4 days and continues to fade to 7A as the flower matures. The red coloration in the basal portion of the ray flowers extends approximately 5 mm from the point of attachment to the disk flowers.

Disk flowers: (Androcoecium and gynoecium).

*Quantity of florets.*—Numerous.

*Shape.*—Tubular.

*Size.*—About 7 mm in length and 1 mm in width.

*Color.*—Tip of petals are 15A tinged with 184A, lower (non-visible portion is 138B).

Reproductive organs:

*Gynoecium.*—Pistil is 4 mm in length and 0.3 mm in width, style is 166C in color, bifid stigma is 166A in color. Ovary is triangular in shape, inferior, single-celled, 4 mm in length and 2 mm in width, 71A in color with the top 1 mm 200A.

*Androcoecium.*—5 stamens, fused, 2 mm in length and 0.25 mm in width, 166A in color, pollen is moderately abundant and 12A in color.

*Fruit.*—An achene, 4 mm in length and 1 mm in width, 200C in color.

*Seeds.*—Seeds are produced and appear to be fertile, however they are not collected or characterized.

I claim:

1. A new and distinct cultivar of Heliopsis plant named 'Prairie Sunset' substantially as herein illustrated and described.

* * * * *

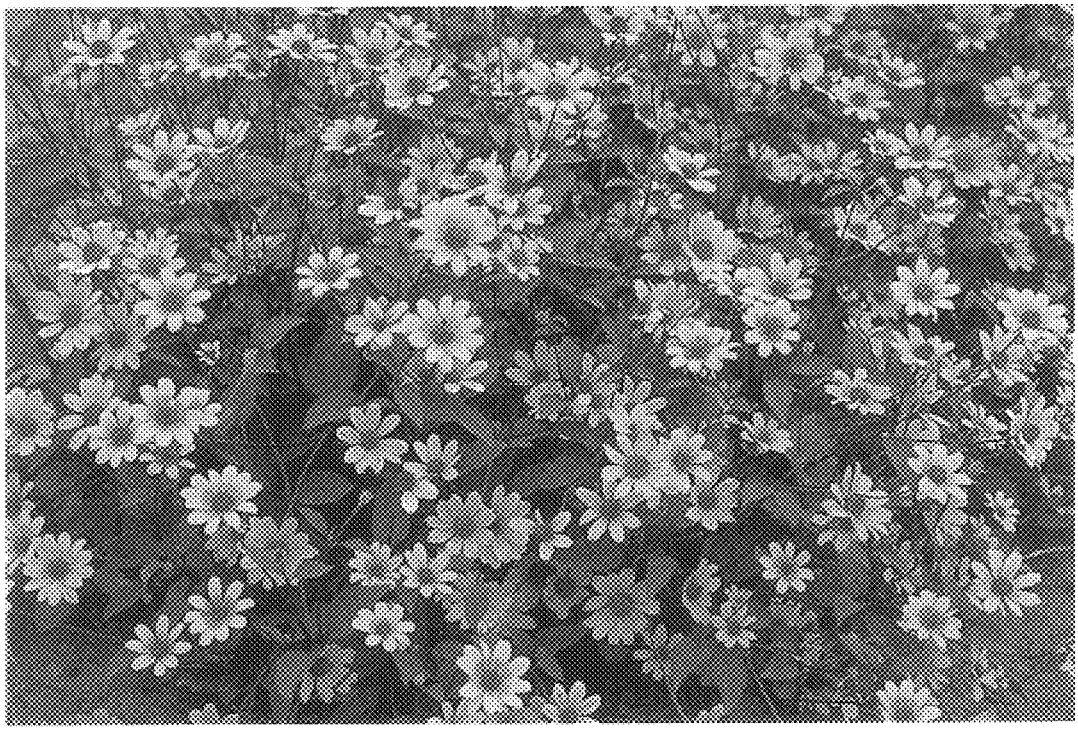
Figure One

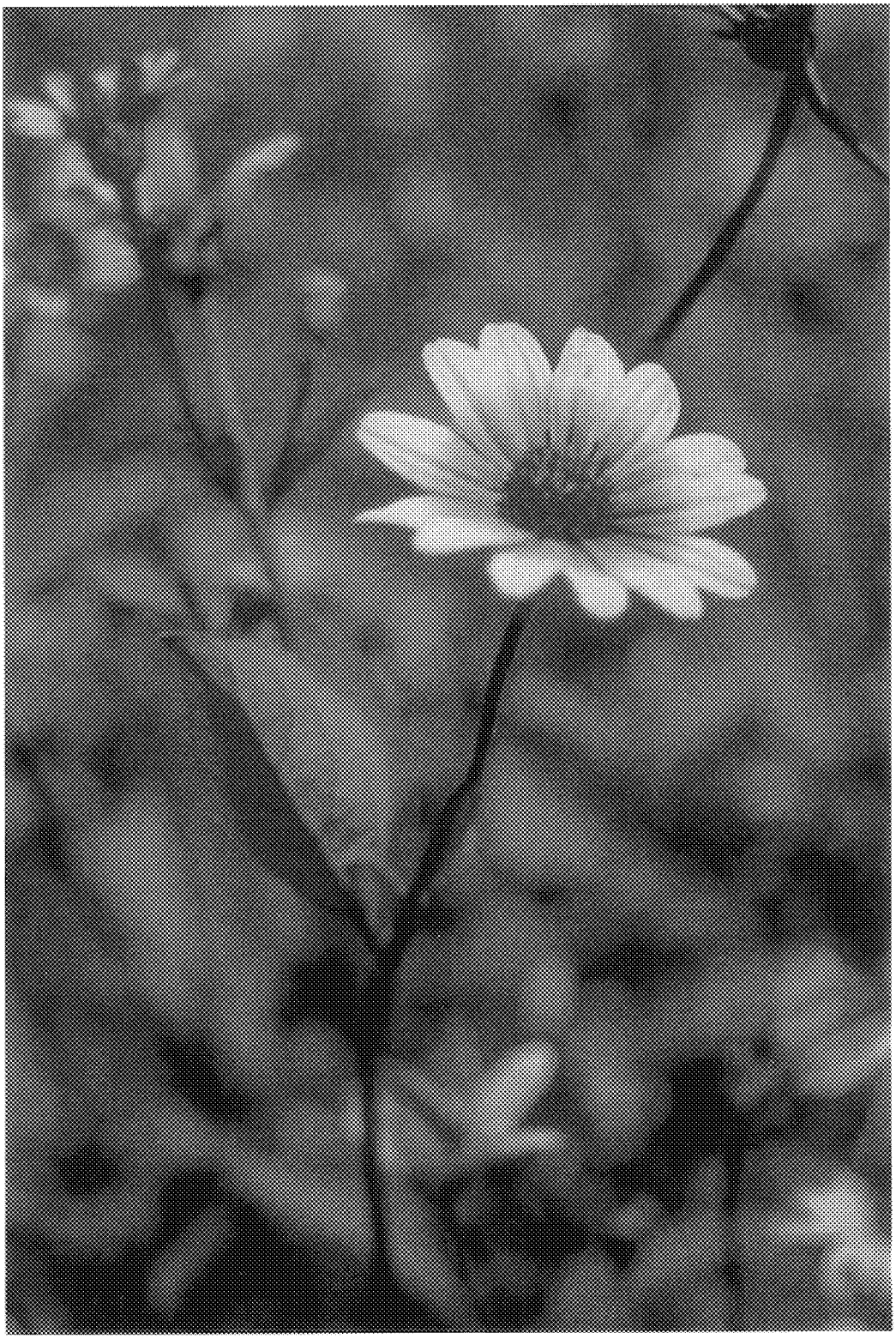
Figure Two

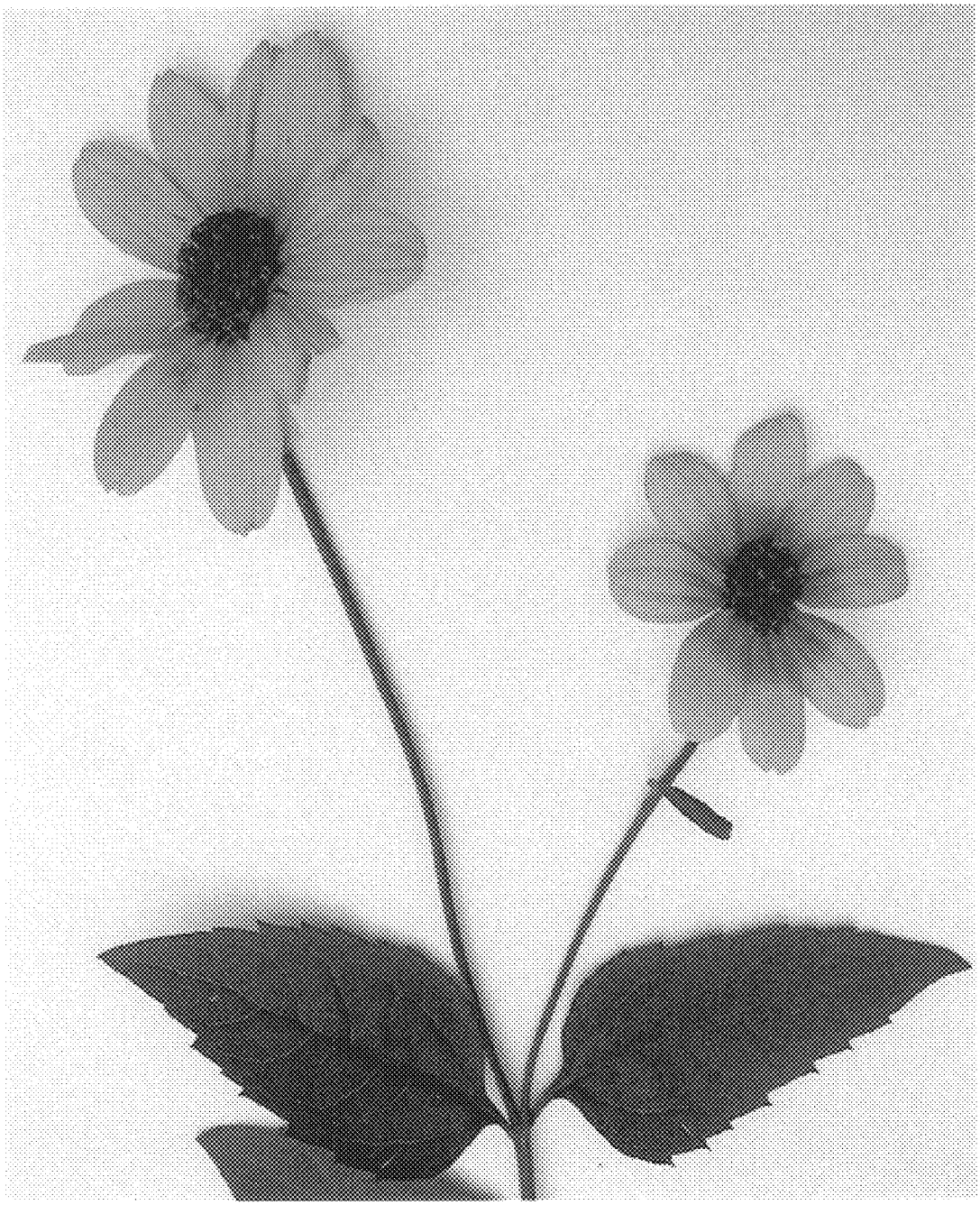
Figure Three